(12) United States Patent
Nagy et al.

(10) Patent No.: US 9,829,327 B2
(45) Date of Patent: Nov. 28, 2017

(54) METHOD FOR PLANNING A ROUTE FOR PHYSICAL TRAINING PURPOSES

(71) Applicant: GPS TUNER KFT, Budapest (HU)

(72) Inventors: Tamas Nagy, Debrecen (HU); Gabor Tarnok, Budakalasz (HU)

(73) Assignee: GPS TUNER KFT., Budapest (HU)

( * ) Notice: Subject to any disclaimer, the term of this patent is extended or adjusted under 35 U.S.C. 154(b) by 0 days.

(21) Appl. No.: 14/914,631

(22) PCT Filed: Aug. 7, 2014

(86) PCT No.: PCT/HU2014/000065
§ 371 (c)(1),
(2) Date: Feb. 25, 2016

(87) PCT Pub. No.: WO2015/022556
PCT Pub. Date: Feb. 19, 2015

(65) Prior Publication Data
US 2016/0209225 A1  Jul. 21, 2016

(30) Foreign Application Priority Data

Aug. 15, 2013 (HU) ..................... 1300487

(51) Int. Cl.
*A63B 24/00* (2006.01)
*G01C 21/34* (2006.01)
(Continued)

(52) U.S. Cl.
CPC ...... *G01C 21/3453* (2013.01); *A61B 5/02405* (2013.01); *A61B 5/1112* (2013.01);
(Continued)

(58) Field of Classification Search
CPC combination set(s) only.
See application file for complete search history.

(56) References Cited

U.S. PATENT DOCUMENTS 5,318,487 A * 6/1994 Golen ............... A61B 5/222
                                          482/3
6,450,922 B1 * 9/2002 Henderson ......... A63B 24/0006
                                          482/4
(Continued)

OTHER PUBLICATIONS

International Search Report issued in International application No. PCT/HU2014/000065, dated Jan. 9, 2015.

*Primary Examiner* — Edward J Pipala
(74) *Attorney, Agent, or Firm* — Handal & Morofsky LLC

(57) ABSTRACT

Method of route planning for physical training, wherein the heart rate of the subject should be kept within a permitted range. Prior to route planning, map data including starting and target points and altitude data are stored. A load profile is created by measuring the heart rate of the subject along routes of different steepness and storing the data in an electronic table, taking into account the required effort and whether the subject could have partially regenerated. The route planning includes searching and selecting a possible route, dividing the route into segments of steepness, and determining the costs based on the steepness data. The cost represents the load when the subject takes that section. Next, expected heart rate is calculated and it is determined whether it will remain in the permitted range along the whole first route. If the heart rate will be in the permitted range, the route is permitted, if not, the steps are repeated for subsequent possible routes where the heart rate in the associated route will remain in the permitted range.

6 Claims, 5 Drawing Sheets

Figure 1:
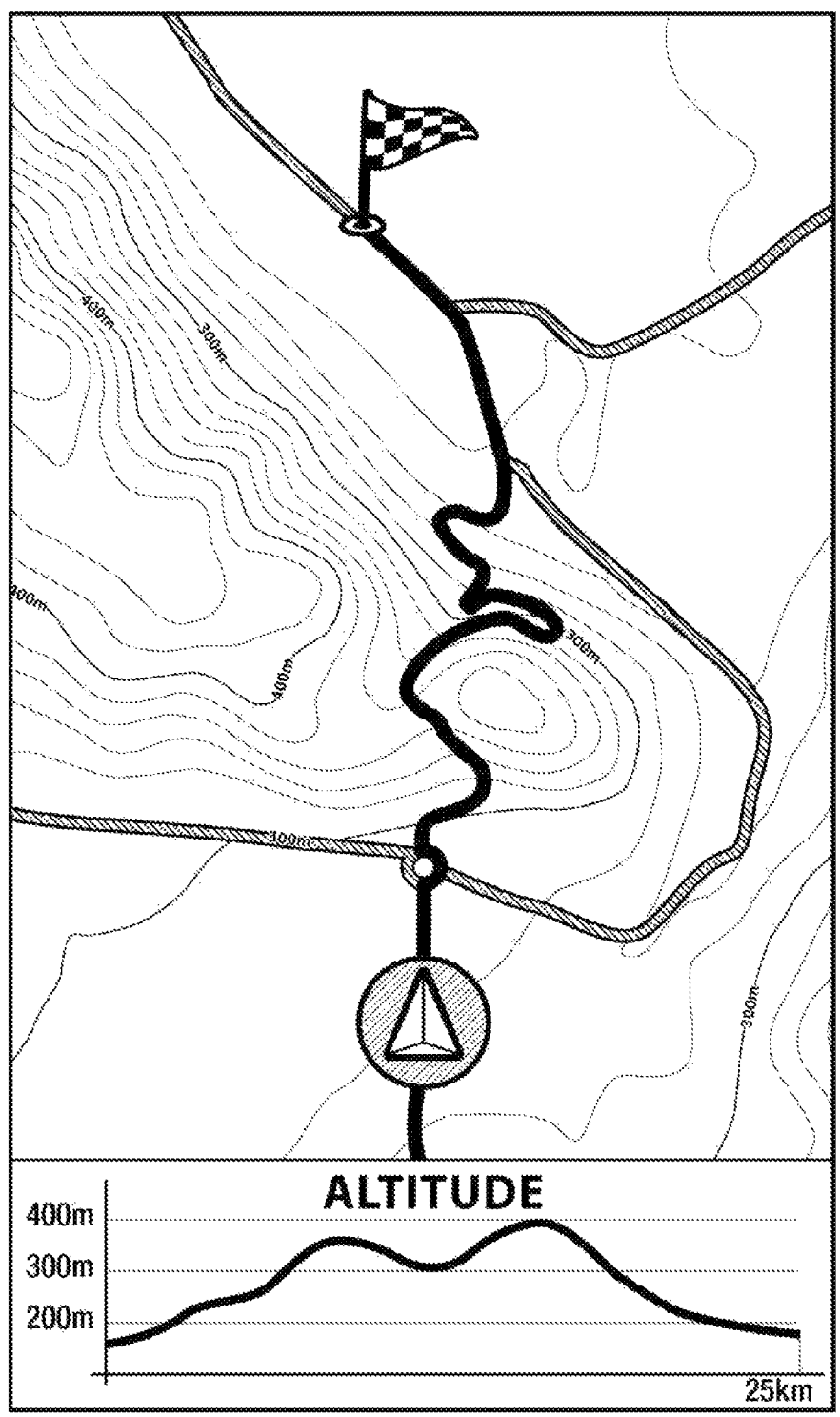

(51) Int. Cl.
*G06F 19/00* (2011.01)
*A61B 5/024* (2006.01)
*A61B 5/11* (2006.01)
*A61B 5/18* (2006.01)
*A61B 5/00* (2006.01)
*G01C 21/20* (2006.01)

(52) U.S. Cl.
CPC .............. *A61B 5/18* (2013.01); *A61B 5/7275* (2013.01); *A63B 24/0062* (2013.01); *A63B 24/0075* (2013.01); *G01C 21/20* (2013.01); *G01C 21/3484* (2013.01); *G06F 19/3481* (2013.01)

(56) References Cited

U.S. PATENT DOCUMENTS

| | | | |
|---|---|---|---|
| 7,357,209 B2* | 4/2008 | Kokatsu | A63B 22/0605 180/206.2 |
| 2010/0022352 A1 | 1/2010 | Kasama | |
| 2010/0198453 A1* | 8/2010 | Dorogusker | A63B 24/0062 701/31.4 |
| 2011/0054779 A1 | 3/2011 | Kim et al. | |
| 2011/0172059 A1* | 7/2011 | Watterson | A63B 22/02 482/5 |
| 2011/0254673 A1* | 10/2011 | Jean | B62M 6/45 340/432 |
| 2012/0083954 A1* | 4/2012 | Aoki | B62M 6/45 701/22 |
| 2012/0185164 A1 | 7/2012 | McCoy | |
| 2012/0329593 A1* | 12/2012 | Larrabee | B64C 39/024 475/5 |
| 2013/0237778 A1* | 9/2013 | Rouquette | A61B 5/02438 600/301 |
| 2013/0297201 A1* | 11/2013 | Van Hende | G01C 21/3407 701/425 |
| 2014/0222268 A1* | 8/2014 | Tsuchizawa | B60L 15/20 701/22 |
| 2016/0039496 A1* | 2/2016 | Hancock | G01S 19/19 701/60 |

* cited by examiner

METHOD FOR PLANNING A ROUTE FOR PHYSICAL TRAINING PURPOSES

TECHNICAL FIELD

The invention relates to a method for planning a route for physical training purposes, for navigation in given cases and if required and for re-planning the previously planned route.

CROSS REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

For running and riding a bicycle and for other spare time sports, many people use GPS based navigation devices and devices recording the route. The target point of the route of the physical training can be set by these devices and the GPS based systems help the performer of the training, i.e., the training subject, to move along the predetermined route, in given cases these devices record the route and certain parameters along the way. However, the GPS-based navigation systems have not been created to be used for physical training purposes, but for navigating one from a given starting point to a fixed target point. If there is more than one routes running to the target point, the navigation system, based on some sort of priority principle, suggests options to choose from the various possible routes. Such principle, for instance, is the shortest route, the fastest route[,] or avoiding certain types of roads, etc.

However, in case of physical training, reaching a target point may not be of a priority, in many cases the starting point and the finishing point coincide with each other, it is important for the person performing the physical training to move along a route satisfactory for his or her physical training needs either by running or by riding a bicycle.

It is a known fact that during physical training, the heart rate is an important parameter. In many cases it is an aim to keep the heart rate within a certain range, at the same time, overdoing the training and the associated too high heart rate may also be harmful.

The training equipments used in gyms have been monitoring and displaying the heart rate for a long time. U.S. Pat. No. 4,566,461 describes a device and method, which is based on the monitoring of the heart rate. For ensuring an appropriate heart frequency the monitor of the device gives instructions for the person performing the physical training (the runner, in a given case) to increase the speed or reduce the speed in order to keep the heart rate close to the allowed maximum. The device disregards the route covered by the runner, the landscape, at the same time, it is burdensome for the person performing the physical training to follow the continuous instructions and it is also unnecessarily tiring to pay continuous attention to the monitor.

U.S. Pat. No. 8,360,936 B2 is similar to the above publication, however it is a training equipment, which determines different zones based on the heart rate, and it displays such zones for the person performing the physical training with different colors. The aim of the equipment is to ensure a physical training controlled by heart rate.

EP 0925096 introduces a training equipment, which, based on heart rate monitoring, controls the load and, as a result, executes the optimal training program.

In document WO2013/075072a method and equipment is described, which, for training purposes, primarily in the case of running along a navigated route, monitors the status of the body and it signals, in case it finds that along the navigated route the recourse of the body increases above the allowed load. In such a case, it re-plans the route or suggests an easier route for the person performing the training.

The basis of the method is the so called cost determination, which is carried out for certain sections of the navigated route (which have consistent difficulty level from a load perspective), moreover, the costs are summed up for the entire route. The definition of cost is rather abstract based on the mentioned document, however, it can be stated that the fitness of certain people is taken into consideration, as well as one or more measured health parameters of the body (primarily the heart rate) depending on the amount of load, as well as the person's age and capabilities. These parameters are taken into consideration as weighted factors, and the basic data are stored based on data gained pursuant to the examination of a number of persons depending on the difficulty level of the landscape. The publication, in the course of the valuation of the data, takes into consideration the outer temperature, the weather conditions and suggests a "self-learning" system, which, based on the series of the previously measured data, refine and update the stored data.

Based on the set out, measured and stored quantities, the publication does not specify the definition of cost and how the cost data is measured and totalized, pursuant to which it provides an estimate for the entire route.

Based on the publication it is distinct, that in the course of the determination of the cost the calculation is done based on the measured data and disregards a number of important circumstances, which are basic parameters of the training and, therefore, affect the accuracy and reliability of the estimations. From those, the following main factors shall be mentioned:

The training is a continuous effort, during which the extent of the load may change, at the same time the body naturally gets tired as a result of the recourse, i.e., after a prior given load the loadability of the body may decrease both in terms of length of the training time and energy, as opposed to in a relaxed state. The load, if it is taken into consideration in the form of a "cost", will provide different values at the beginning, in the middle of or at the end of the training, and therefore, in the course of the calculations, the length and extent of the previous load cannot be disregarded.

The human body, however, is capable of being regenerated to a certain extent in the course of a load, i.e., if, in the course of the training, there are sections with less load or specifically relaxing sections (for example, during riding a bicycle the horizontal landscape or downhill can be considered as a relaxing section) pursuant to a partial regeneration the loadability of the person may increase, as opposed to where there is no regeneration section in the course of the training.

Finally, it should be noted that in the course of the training, particularly, if it is being carried out on an unknown landscape, there may be certain sections, which exceed the normal loadability of the person performing the training, therefore, such section should be avoided even if the cost calculated for the entire route would fall within the range that is permitted for the given person.

The training along a planned navigated route comes into play with respect to bicycle trainings, but in many cases, as well as in the course of running/walking. In the case of bicycles, the use of the electric bicycles is very popular, where the ratio of the human drive and the supplementary electric drive may be adjusted, moreover, these ratios may be set electronically.

For the persons performing the training the most comfortable and effective would be if they would be able to run or ride a bicycle on such a landscape or route, which is capable of accommodating their training concepts to the maximum.

The heart rate is known to be the body's reaction to the load, and it is practical for everybody to do training according to his or her own fitness and health status in a way so that the heart rate is kept within a certain range, and longer overloads (when the heart frequency exceeds the permitted threshold or the threshold proposed from a health perspective) should be avoided.

SUMMARY OF THE INVENTION

The primary object of the present invention is to create a more accurate and reliable planning method, which is capable of planning a route for the purposes of a physical training during which the heart rate of the training subject will be kept within a wished and permitted range along the whole planned route and which takes into account the natural properties of human body including that one gets tired and less loadable as time advanced during a training, and also that the movements might have sections with smaller loads that allow the body to have a rest and regenerate at a certain extent.

A further object of the invention is to actually navigate the training subject along the route planned and at the same time to monitor his or her actual heart rate all through the training, and in case it is needed, to intervene by changing the route or by other means with the accuracy provided by taking into account the previously described human loadability and regeneration properties.

As we know the steepness and the characteristics of the planned route as well as the load relevant to the person performing the training, and depending on the load the heart rate of the person performing the training can be more or less known or can be measured in advance, it is possible that in a given moment, the person's tiredness or the incidental change in his or her health state or for other external reasons, the heart rate does not meet the expectations, and the heart rate is higher than it is expected in the course of a certain section of the training, but falls within the permitted range. In such a case it is useful to calculate the expected load on the basis of the route, and consider whether or not the expected load would exceed the given permitted range of the heart rate, i.e., whether or not the permitted range of the heart rate will be exceeded by the expected load, in other words, whether it can be expected that the heart rate will exceed the permitted threshold in the course of the planned route. If we experience such a risk with load estimation made in regular intervals, it is possible to re-plan the previously planned route, where the re-planned route would be less steep, its total fall would be less, and as a result, the heart rate may be kept within the permitted range in the course of a re-planned route.

For solving the above objectives a method of route planning has been provided for physical training purposes, wherein during movement along the planned route the heart rate of the person performing the training should be kept within a given range; and therefore the map data of the surrounding area of a starting and a target point, including the associated altitude data, are stored in an electronic form in a navigation device; the measured data of the person performing the training, relating to the load along routes of different steepness as correlated with his or her heart rate data, as a load profile characteristic of such person, is included in an electronic table and stored in the device; possible routes between said starting and target points are searched for; along such routes systematic examinations are carried out to find out whether or not these possible routes are suitable for the person performing the training; the first one of such possible routes is divided into sections that have respective constant steepness or inclination; the respective costs typical of each section are determined based on the steepness or inclination data of the section by using the said load profile; and from the costs so determined conclusion is drawn by calculation whether or not in the course of the movement of the person performing the training along a given route, the load on such person will be within the permitted range; if the result is affirmative, the road is accepted and if the result is negative the steps and calculations will be repeated until an acceptable route is found; and according to the invention the method is further refined in a manner that when determining the load profile of the person performing the training, besides the data associated with the load under examination, the time elapsed since the beginning of the training and the total load during said elapsed time is also taken into consideration; and it is also taken into consideration whether there was a previous section in the course of the route wherein the course of moving along such section the required level of effort has decreased compared to previous loads and the body of the person performing the training could then have a chance to at least get partially regenerated; furthermore the maximum threshold load on the person performing the training is determined and stored in the device; and two costs are applied to each section, from which the first cost is the quantity typical of the effort made in the course of the given section, and the second cost is the weighted cost (the cost weighted with the prior load and the regeneration, if applicable) arising in the course of a given section. In the course of the calculation-conclusion step, the first costs are totalized for the entire route and the route is regarded acceptable, if the totalized cost is smaller than the cost associated with the measured threshold load. In addition, with respect to each section the second costs are compared to the appropriate section of the load profile, and if the second cost exceeds the amount permitted for the given section, the route in question is not accepted and re-planning of the route is commenced.

In order to increase accuracy, the load profile is recorded based on the results of a series of measurements conducted at different times, practically, by the use of a self-learning program.

For practical reasons, the person performing the training is navigated by the navigation device along the accepted planned route.

In case the starting point and the target point would coincide with each other, the route is planned by taking into consideration a predetermined training time and/or heart rate range.

In a preferable embodiment the heart rate of the person performing the training is measured continuously or within small intervals in the course of the movement along the navigated route and then this is compared to the expected values determined taking into consideration the load profile, and if in the measured heart rate values a definite change is found compared to the expected value, then stored values of the load profile is weighted, i.e., the cost data is increased or decreased proportionately, and the calculation of the costs for the reaming part of the route is repeated by using the modified load profile. In such a case if an overload is calculated, then the person performing the training is notified about it and a new route is proposed by re-planning the route.

If the training is carried out by the person performing the training by using a vehicle equipped with a partial electric drive, in which the proportion of the electric and human drive components can be adjusted; and when along one or more sections of the planned route the cost calculation indicates that the required energy would exceed the permissible load with respect to such person, then instead of re-planning of the route the ratio of the electric drive component is increased by the required extent compared to the human contribution component or the person is notified about the need to increase this ratio.

As a result of the use of the method according to the invention much more accurate and reliable results are obtained as opposed to the previously used methods, due to the fact that, in the course of the calculation of the cost, more basic characteristics of the human body are taken into consideration and it is also rarer that overload occurs in the course of traveling along the navigated route.

DETAILED DESCRIPTION OF THE INVENTION

Figure 2:
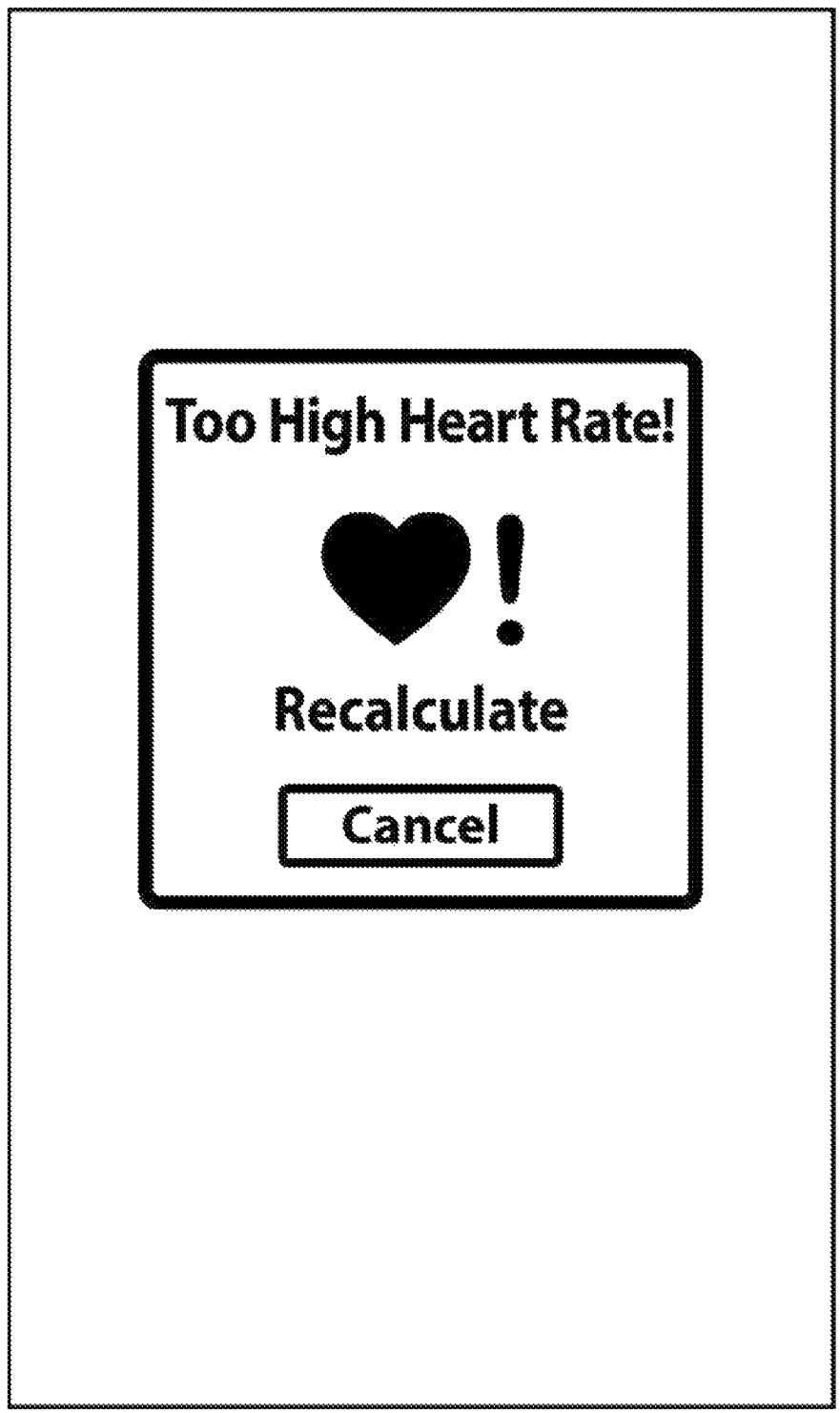
Figure 3:
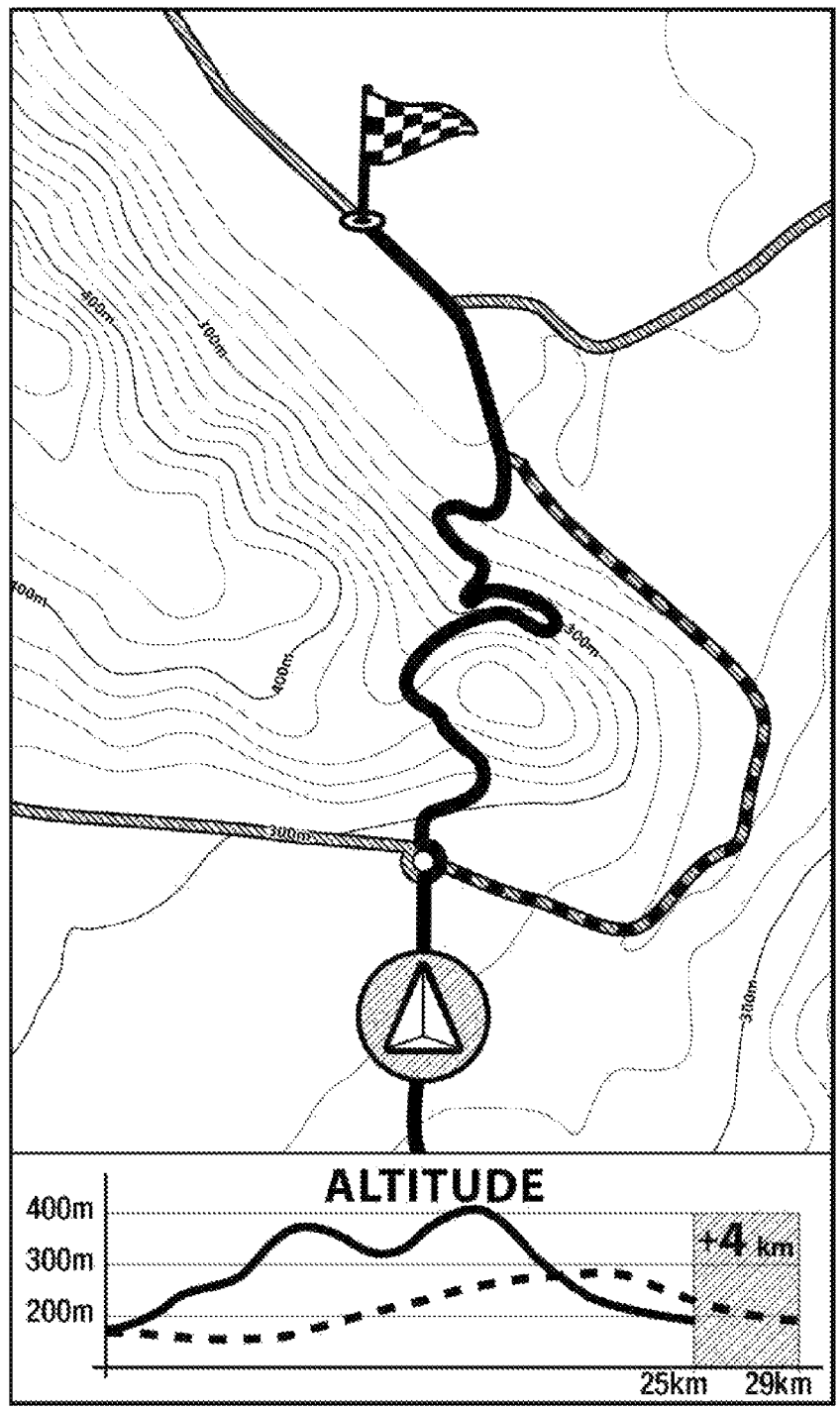
Figure 4:
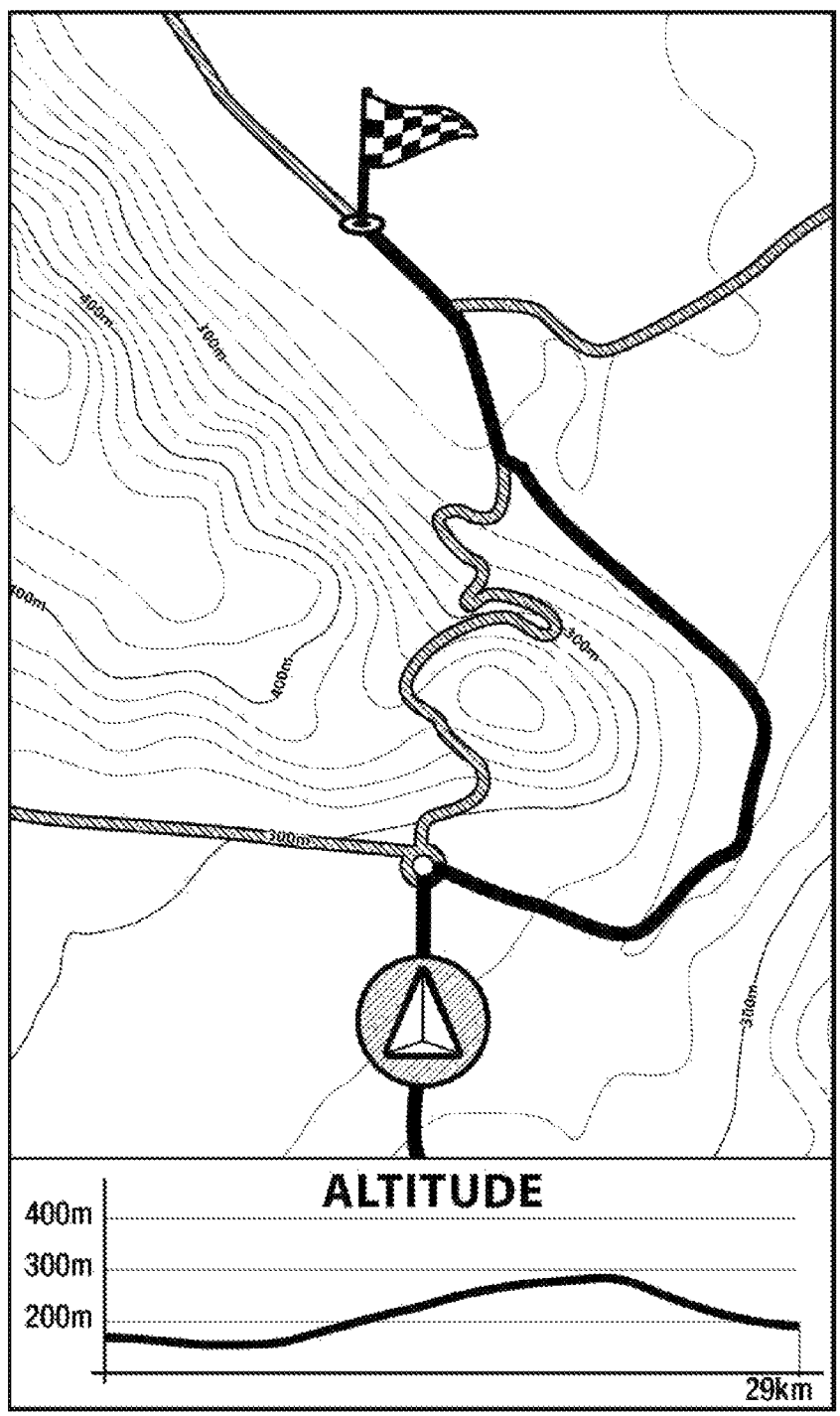

The method according to the invention is further introduced in detail below in connection with examples, in which reference will be made to the accompanying drawings: In the drawing:

FIG. 1—shows a route planned by the method according to related to the invention as visible on the display;

FIG. 2—shows display view expected to be shown when the heart rate is exceeded;

FIG. 3—shows a proposal for re-planning the route;

FIG. 4—shows the acceptance of the re-planned route; and

Figure 5:
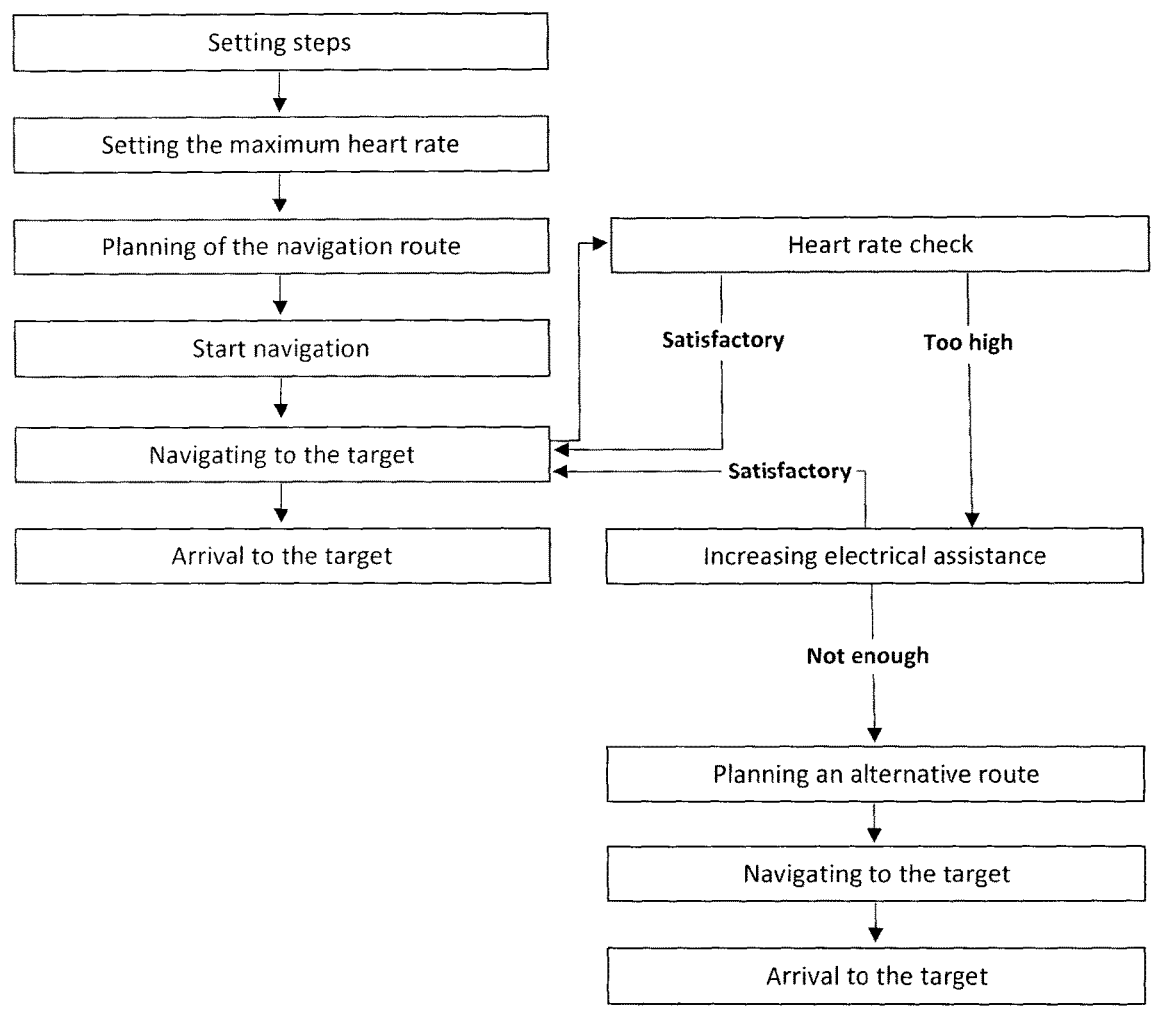

FIG. 5—is a flowchart of the method according to the invention.

DETAILED DESCRIPTION OF THE INVENTION

In the course of the method, first the driver's load profile should be thoroughly determined. Load profile is determined for the given person, who is subject to various loads corresponding to his or her training, in the meantime the heart rate and the change of the heart rate is measured. When determining the load profile the time elapsed from the beginning of the load is taken into consideration, the load (primarily the steepness, the length and the speed of the route), and the heart rate are saved, and the time associated with the saved data and elapsed since the beginning of the training is stored as well. Entering the load profile is quite a time consuming exercise, because it is done pursuant to a number of repeated and accrued loads. It is known that in the case of equal or significantly similar load the heart rate, following a given integrated total load typical of the given person's fitness, suddenly starts to increase. Training should be concluded at such time at the latest. The energy affected until the mentioned moment of time is actually the loadability of the given person measured at a given point in time. Such loadability, as all of the previously affected energy, is not a constant number, but is strongly dependent on the time profile of the load. In order to determine this, the examination is carried out repeatedly with undulating load in time. Between the repetitions the examined driver is allowed to be fully regenerated, i.e., there is a rather big interval between two repetitions. Pursuant to these repeated examinations, the extent of the regeneration as a result of a larger load followed by a smaller load is determined, i.e., the extent of the increase (or decrease) of the total energy, affected until the heart rate significantly increases, due to the temporarily smaller load. It can be also measured that during the time of the load the heart is within a given range in the starting phase when a larger load is applied. However, corresponding load in a later stage of the training is not permissible, i.e., the extent of the loadability decreases by the lapse of time in the course of the training. If there is not enough time or there is no opportunity for saving the load profile, the mentioned data is measured during the actual training carried out on various landscapes and the data typical of the examined profile is refined by a self-learning program based on the measured data. Features changing over time mean features, which include the dependency of the loadability of the driver from the training time, his or her ability to regenerate in the case of the changing of the load and the number associated with the total energy affected related to the significant increase of the heart rate, which changes in the case of undulating load to various extents. Based on the knowledge of the above data, the expected heart rate of the driver on a route to be planned can be estimated fairly accurately.

In addition to the data specified herein, the existence of such a navigation system is assumed, which stores the coordinates of the environment as well as the altitude data of the various points in its electronic database.

Following the storing of the mentioned data related to the load profile and the map data, the operator (or his or her trainer) sets the starting point (sometimes it is the actual location) and the target point. If the target is not to reach a certain geographical location, but, for example, to return to the starting point within a certain training time, then in addition to setting the starting point and the target point, the expected duration of the training, for example, or the length of the route, should also be set. If the operator has an individualized training program, the parameters of such program can be also set (for example, the changing of the heart frequency range and the permitted maximum thereof). In the lack of a training program, it should at least be assumed about the operator, that he or she knows the range within which the heart rate should be kept during the training and the maximum number of the permissible heart rate.

According to the settings, the first step is route planning. With respect to route planning, the load-heart rate data included in the electronically stored table is taken into consideration. It is known that navigation devices, based on certain parameters, find the possible route between the starting point and the target point.

In our case, in the course of the route planning, the load profile is calculated for each possible route. This is done with the use of the Dijkstra algorithm. The mentioned coordinates of the routes are included in the map database, namely, the peak points with respect to each route. Peakpoints are such points of the route, at which certain parameters typical of the route, change. Such parameter is typically the change of the steepness of the route. The Dijkstra algorithm uses graphs. Here the peak points of the graphs are the mentioned peak points, the edges of the graphs are the edges between the peak points. The algorithm applies a "cost" to each edge, which application is determined in accordance with the previously mentioned principles. In the principle case, the cost consists of the energy consumption of the edge with the known steepness and length weighted with the preferred speed during the training, and a second cost-type parameter is also applied to this, namely, the numbers of the heart frequency, which depends on not only the energy consumption, but also from the amount of the total costs prior to a given edge, how much time elapsed and whether there was an opportunity to a partial regeneration prior to a given edge. Taking into consideration this second cost parameter it can be decided whether or not along a given edge the driver's heart frequency can be expected to stay within the permitted threshold. Taking into consideration the antecedents with respect to each section, it is shown whether the given section can be permissibly covered by the driver. However, by the end of the section all of the first costs from the beginning are known and it can be verified whether or not the value thereof reaches the total value of all of the permitted energy. In the course of the route planning the first and second costs are calculated from the starting point for each section, and if, along the route until the target point the total amount of the first costs does not exceed the number of the permitted total energy and with respect to each section none of the second costs reach the maximum threshold, then the examined possible route can be chosen and this will be the suggested route for the driver.

On FIG. 1 the planned route is displayed on the monitor of the navigation device, where the triangle means the starting point and the flag means the target point. The planned route is indicated with bold line. The level lines as well as another route are also shown on this picture. The level diagram between the two end points is separately indicated at the bottom of the picture.

If the driver accepts the planned and suggested route, the driver is navigated by the navigation device with the usual navigation instructions and drawings until the target point is reached.

According to a second aspect of the invention, the method is not completed with the planning of the route optimally appropriate for the given training target, as in the course of traveling along the route, the actual heart rate is continuously measured. There are a number of health, human or other circumstances, as a result of which the measured heart rate of the person performing the training, who is called the driver herein, deviates from the measures taken into consideration in the course of the calculations. Along the route, within given intervals, for example within 0.5-2 minute intervals not only the heart rate is measured, but the range of the heart rate is also calculated again with the use of the Dijkstra algorithm for the remaining part of the route. This calculation deviates from the route planning, as here there is actual knowledge about the measure of the load with respect to the route already covered and the heart rate resulted therefrom. If the tiredness of the driver based on the actually measured heart rate is different from the tiredness taken into consideration in the course of the calculation, the cost calculation should be modified accordingly, i.e., the loadability is modified accordingly. It is noted that for such modification significant deviations changing in tendency (not random deviations) are taken into consideration, i.e., modification takes place only if there are similar deviations from the originally planned in more cycles followed by each other.

If the total amount of the first costs or second costs determined pursuant to the modifications calculated for the originally planned route indicate that the heart rate reaches or exceeds the permitted maximum threshold at a certain point in the course of the remaining part of the route, the driver is sufficiently notified about it. Such a possible display is shown on FIG. 2.

The most practical version of the method in such a case the route, is re-planned and it is examined whether there is another route leading to the target, for example the fall is smaller or there are more moderate sections appropriate for regeneration, and therefore, it can be expected that moving along such route the driver's heart rate will stay within the wished range. In the course of the re-planning of the route the landscape of the various sections of the route are taken into consideration with special care, as besides the speed, this has the most effect on the required effort and as a result, the heart rate.

FIG. 3 indicates with dashed lines a re-planned detour, which means a much less load. The dashed line of the horizon diagram also qualifies as such a re-planned route. If the driver accepts the re-planned route, the navigation will continue on the re-planned route and such route will become the basic route of the navigation. FIG. 4 indicates such a case.

If the re-planning does not have any results, it is displayed for the driver that it is expected that he or she will not be able to cover such route. The driver may respond to this by decreasing the speed or, in the case of electric bicycles, adjusting the ratio between the electric and human drive, so that there will be more load on the electric drive. In the course of the calculations the shortfall of the need of the human energy becomes known. From this it can be determined how much energy should be provided by the electric drive of the bicycle for curing the shortfall. In such a case it is practical to increase the minimum electric power by 10-20% of the minimum required electric drive. Naturally, in case of such an electric "supplement" there is no need to re-plan the route. If the extent of the supplement can be electronically controlled, then such measure can be set automatically with the device used for the method. Obviously, in such a case the measurement and the calculations should be continuously repeated and if the driver got regenerated or the extent of the supplement was not sufficient, the ratio can be set again.

The specialty of the method related to the invention is that the accuracy of the estimations of the costs have been improved compared to the known solutions. This is obvious, as the connection between the load and the expected heart rate is determined by taking into consideration the tiredness and regeneration occurring in the course of the previous route. There is a double condition for permitting a route. More specifically, for each section it is examined, taking into consideration tiredness, whether moving along such section constitutes a load, which would increase the heart rate above the permitted maximum range. At the same time it also determines the total energy consumed for the route covered so far, predetermines the energy to be used for the remaining sections of the route and if the totalized amount of these does not reach the appropriate level of fitness, then it allows to move further along the route. As a result, expected overloading can be effectively avoided and pursuant to the re-planning of the route for a currently tired or slightly stuporous driver the method suggests a load that is suitable for his or her current state and the associated route.

FIG. 5 summarizes the flowchart of the method.

The first three steps basically are the most important and sufficient sections of the method, which consists of the planning of the route suitable for the given circumstances and displaying of such route for the driver.

Following this, the driver is navigated along the planned route by the navigation system.

Moving along the route, the heart rate is measured in regular intervals and for the remaining part of the route prediction calculation is made, i.e., it is examined whether or not the heart rate would stay within the permitted range as a result of the effect of moving along the route on the heart rate. If so, sampling and the prediction calculation is repeated until the target point is reached in the given intervals.

If the prediction calculation predicts that the heart rate will increase above the permitted range, then some sort of intervention follows. In FIG. 5 such a very rare case is shown, where the driver trains with an electric bicycle and it is possible to increase the proportion of the electric power. Due to this automatic option it is unnecessary to re-plan the route.

If such an option is not available or not sufficient, then an alternative road is searched for, along which the load keeps the heart rate within the permitted range. Then by accepting this route the driver is navigated along this new route to the target point.

Pursuant to the method related to the invention the quality of outdoor training significantly improves, as besides the navigation the load set by the driver is also taken into consideration and a route is suggested to the driver, which will ensure for the driver the his/her heart rate will remain within the permitted range when taking this route. The device necessary for the execution of the method can be an off-line, practically, mobile device which, except for the position data necessary for the navigation, does not require external data connection.

The invention claimed is:

1. Method of route planning for physical training purposes, wherein during movement along a planned route the heart rate of the training subject should be kept within a permitted range; comprising the steps of:
   as preparatory steps prior to the actual route planning:
      storing in a navigation device map data of an area concerned that includes required starting and target points, the map data include also altitude data;
      determining a load profile of the subject including:
         measuring the heart rate of the subject along routes of different steepness;
         storing the so obtained data in an electronic table stored in the device;
   the actual route planning includes the further steps of:
      searching possible routes between said starting and target points;
      selecting a first one of the possible routes and dividing the first possible route into segments that have respective constant steepness;
      determining the respective costs typical of each section based on the steepness data of the section using the table of said stored load profile, wherein the cost represents the load when the subject takes that section;
      calculating from the determined cost values in the course of the movement of the subject proceeding along said first possible route his expected heart rate;
      examining whether the expected heart rate will remain in the permitted range along the whole first route;
      accepting the first route as planned route if the examination shows that the heart rate will be in the permitted range; and
      repeating the planning steps for subsequent possible routes as long as the examination at a route shows that the heart rate in the associated route will remain in the permitted ranged, and accepting that route as the planned routed, characterized in, that during the step of determining the load profile the time elapsed since the beginning of the movement is also stored in said table, and said determination step is carried out repeatedly and the extent of regeneration of the subject is determined as a result of a larger load followed by a smaller load; and at said calculation step of the expected heart rate the cost of any section depends also on the time elapsed since the beginning of the movement and the total load during said elapsed time; and in said calculating step examining at each section whether at the previous section or sections there was a decrease in the required level of effort in which the subject could have partially regenerated and if such is experienced the previously determined regeneration is also taken into account in determining the cost associated with the concerned section.

2. The method as claimed in claim 1, wherein navigating the subject with the navigation device along said accepted planned route.

3. The method as claimed in claim 1, wherein said starting and target points are the same, said route is planned on the basis of a predetermined training time and/or so that the heart rate of the subject remains in the permitted range.

4. The method as claimed in claim 2, wherein during movement along the planned route monitoring the heart rate of the subject and comparing the actual heart rate with the calculated expected value for the given point of the route, and if a definite increase has been experienced, repeating the determination of the costs for the remaining part of the route by using the measured actual heart rate, and if the repeated determination shows that the expected heart rate along the originally planned route would cross said permitted range, notifying the subject about the potential overload.

5. The method as claimed in claim 4, wherein after or instead of said notifying step starting a new search for an alternative route, and if such is found, navigation the subject along this route.

6. The method as claimed in claim 4, wherein the training is carried out by the subject by using a vehicle equipped with a partially electric drive, in which the proportion of the electric and human drive components can be adjusted; and after said notifying step or instead of it increasing the ratio of the electric drive component by the required extent compared to the human contribution component.

* * * * *